US010226264B2

(12) United States Patent
McIntosh et al.

(10) Patent No.: US 10,226,264 B2
(45) Date of Patent: Mar. 12, 2019

(54) APPARATUS AND METHOD FOR DESTRUCTION OF VASCULAR THROMBUS

(75) Inventors: Charles L. McIntosh, Silver Spring, MD (US); Ram H. Paul, Jr., Bloomington, IN (US); Darin G. Schaeffer, Bloomington, IN (US); M. Kem Hawkins, Bloomington, IN (US); Frank J. Fischer, Jr., Bloomington, IN (US); Grant T. Hoffman, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 279 days.

(21) Appl. No.: 13/555,685

(22) Filed: Jul. 23, 2012

(65) Prior Publication Data
US 2013/0023802 A1    Jan. 24, 2013

Related U.S. Application Data

(63) Continuation of application No. PCT/US2011/022672, filed on Jan. 27, 2011.

(60) Provisional application No. 61/299,143, filed on Jan. 28, 2010, provisional application No. 61/366,744, filed on Jul. 22, 2010.

(51) Int. Cl.
*A61H 1/00* (2006.01)
*A61B 17/22* (2006.01)
*A61M 25/10* (2013.01)
*A61M 37/00* (2006.01)

(52) U.S. Cl.
CPC ....... *A61B 17/22004* (2013.01); *A61M 25/10* (2013.01); *A61M 37/0092* (2013.01); *A61B 2017/22001* (2013.01); *A61B 2017/22008* (2013.01); *A61B 2017/22051* (2013.01); *A61B 2017/22088* (2013.01);
(Continued)

(58) Field of Classification Search
CPC .............................. A61N 7/00; A61H 23/0245
USPC ............................................................. 601/2
See application file for complete search history.

(56) References Cited

U.S. PATENT DOCUMENTS 5,421,338 A * 6/1995 Crowley ................ A61B 5/416
                                                        600/463
5,676,692 A * 10/1997 Sanghvi et al. ................ 606/27
(Continued)

FOREIGN PATENT DOCUMENTS

WO     WO 00/18468      4/2000    ............ A61M 37/00
WO     WO 02/062239 A2  8/2002    ............ A61B 17/22
(Continued)

OTHER PUBLICATIONS

International Search Report and Written Opinion of PCT/US2011/022672, dated May 3, 2011.
(Continued)

*Primary Examiner* — Hien Nguyen
(74) *Attorney, Agent, or Firm* — Brinks Gilson & Lione

(57) ABSTRACT

A device for thrombolytic therapy is provided. The device includes an elongate catheter with a distal end portion and a proximal end portion and a first lumen extending through both distal and proximal end portions. The distal end portion of the catheter includes an echogenic tubular potion that defines or surrounds a portion of the first lumen. An expandable balloon coaxially surrounds the tubular portion. The tubular portion additionally includes a plurality of indentations defined upon an outer surface thereof.

22 Claims, 11 Drawing Sheets

(52) U.S. Cl.
CPC .............. *A61B 2017/22089* (2013.01); *A61M 2025/105* (2013.01); *A61M 2025/1013* (2013.01)

(56) References Cited

U.S. PATENT DOCUMENTS

| | | | | |
|---|---|---|---|---|
| 5,807,306 | A * | 9/1998 | Shapland et al. | 604/21 |
| 6,096,000 | A | 8/2000 | Tachibana et al. | 604/20 |
| 2002/0032406 | A1* | 3/2002 | Kusleika | 604/101.02 |
| 2003/0236496 | A1* | 12/2003 | Samson et al. | 604/103.02 |
| 2004/0039332 | A1* | 2/2004 | Kantor | A61M 25/0023 604/103.04 |
| 2004/0225318 | A1* | 11/2004 | Eidenschink et al. | 606/194 |
| 2007/0235899 | A1* | 10/2007 | O'Halloran | A61F 2/958 264/319 |
| 2008/0077085 | A1* | 3/2008 | Eidenschink | A61M 25/10 604/96.01 |
| 2009/0105633 | A1* | 4/2009 | Tachibana | A61K 41/0047 604/20 |
| 2009/0247878 | A1* | 10/2009 | Tanioka | A61B 5/6852 600/462 |
| 2010/0317963 | A1* | 12/2010 | Clancy | A61F 2/95 600/424 |
| 2011/0106054 | A1* | 5/2011 | Osborne | A61B 17/8816 604/518 |

FOREIGN PATENT DOCUMENTS

| | | | | |
|---|---|---|---|---|
| WO | WO 2006/032031 A1 | 3/2006 | | A61M 31/00 |
| WO | WO 2011/094379 A1 | 8/2011 | | A61M 37/00 |

OTHER PUBLICATIONS

EPO Notice of Intention to Grant, EP 11702760.7, dated Jun. 27, 2018, 88 pp.
Examination Report, EP 11702760.7, dated Oct. 31, 2016, 4 pp.
International Preliminary Report on Patentability and Written Opinion for Application No. PCT/US2011/022672, dated Jul. 31, 2012, 8 pp.
Communication Pursuant to Article 94(3) EPC for Application No. 11 702 760.7, dated Oct. 31, 2016, 2 pp.

* cited by examiner

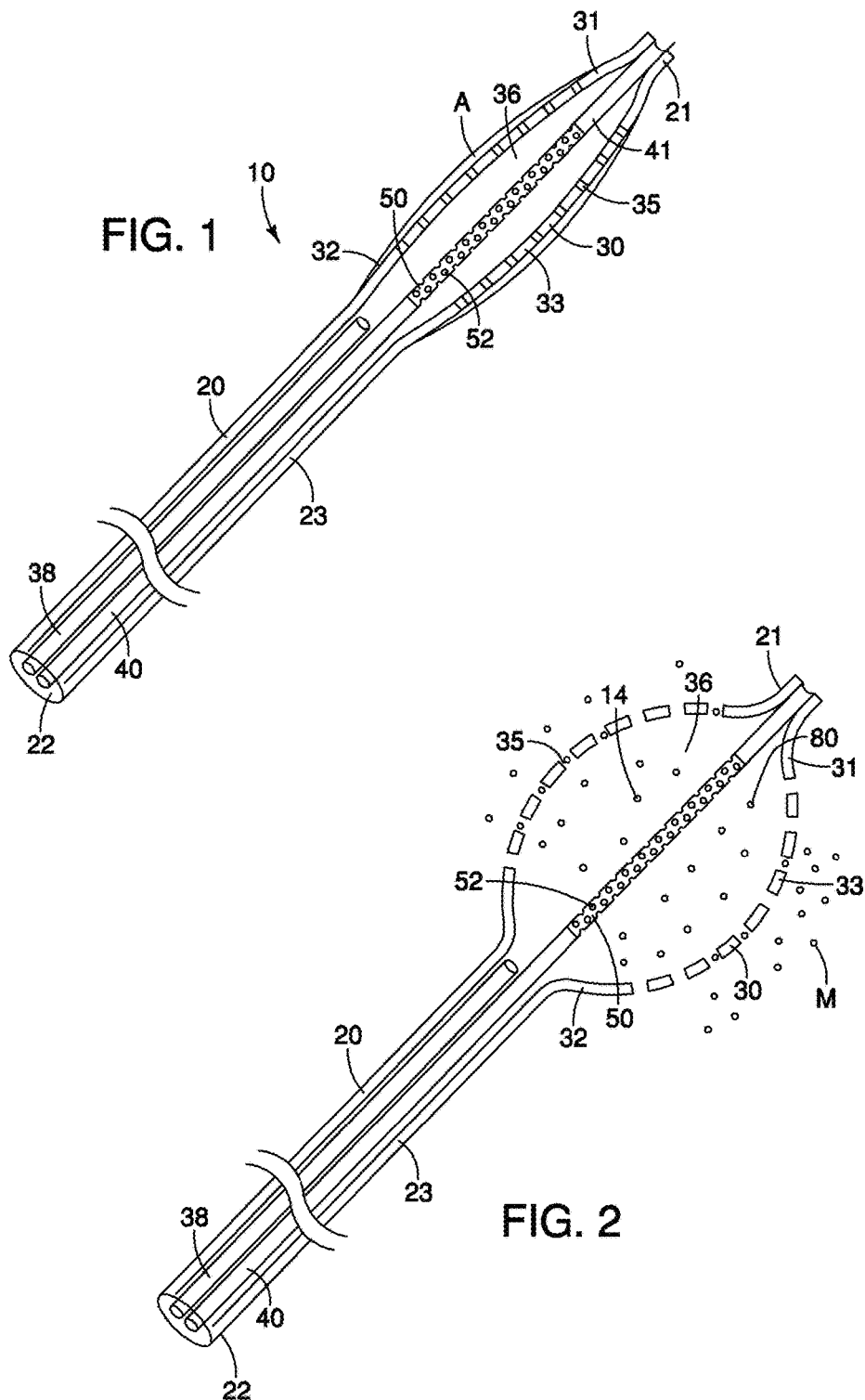

APPARATUS AND METHOD FOR DESTRUCTION OF VASCULAR THROMBUS

This application is a continuation of PCT Application No. PCT/US2011/022672, filed on Jan. 27, 2011 and Published as WO 2011/094379 on Aug. 4, 2011, which claimed priority from U.S. Provisional Application No. 61/299,143, filed on Jan. 28, 2010, and U.S. Provisional Application No. 61/366,744, filed on Jul. 22, 2010, the entirety of which are each hereby fully incorporated by reference herein.

TECHNICAL FIELD

The present disclosure is related to medical devices and more particularly to medical devices adapted to remove or reduce a deep vein thrombosis (DVT), restenosis, or other occlusions disposed within a patient's vasculature. Thrombosis or other types of occlusions are large blood clots formed within the vasculature and fixed to a vessel wall. These clots are known to be created and expand in size in various parts of the anatomy, typically legs in the femoral vein or the popliteal vein, and are typically problematic in trauma patients, orthopedic surgery patients, neurosurgery patients, or in patients having medical conditions requiring bed rest or non-movement, such as during long haul air travel. During and after such medical conditions or situations it is often that large thrombosis formed within the patient's vasculature have a tendency to break free and travel or embolize through the vasculature toward the patient's heart and lungs potentially blocking blood flow into the lungs. In other circumstances, the dislodged portion may be caught within a different portion of the vasculature to substantially or totally occlude blood flow through that portion.

Due to the problematic disruption of localized blood flow (or potential total occlusion of flow) through a localized portion of the patient's vasculature, and the additional dangerous potential of dislodged portions of a thrombosis flowing into the patient's heart or through the pulmonary artery to the lungs, it is often medically necessary to reduce the size of a thrombosis when noted within the vasculature.

BRIEF SUMMARY

A first representative embodiment of the disclosure provides a device for thrombolytic therapy. The device includes an elongate catheter with a distal end portion and a proximal end portion, and a first lumen extending through both the distal and proximal end portions. The distal end portion of the elongate catheter includes a tubular portion that defines or surrounds a portion of the first lumen, and a first expandable balloon coaxially surrounding the tubular portion. The tubular portion includes a plurality of indentations defined upon an outer surface thereof.

The representative embodiment further includes a plurality of indentations that are defined upon an outer surface thereof, wherein the plurality of indentations are located, sized, and shaped to reflect or focus incipient ultrasound energy in a predetermined pattern.

The representative embodiment disclosed above, wherein the plurality of indentations are disposed around substantially an entire outer surface of the tubular portion in spaced relationships.

The representative embodiment above, with a second lumen defined in the catheter and extending through the proximal end portion thereof, wherein the second lumen allows selective fluid communication with a first volume defined by an inner surface of the first balloon and an outer surface of the tubular member.

The representative embodiment above, wherein the first balloon is configured to expand outwardly, but remaining substantially coaxial with the tubular portion, when a pressurized fluid or gas collects within the first volume.

The representative embodiment above, further comprising a third lumen configured to selectively provide fluid communication to a third volume disposed between an inner surface of the first balloon and an outer surface of the second balloon. Wherein the third lumen is configured to inject a microbubble solution or a bioactive agent into the third volume.

The representative embodiment discussed above wherein a surface of the first balloon is coated with a bioactive agent. The bioactive agent is an antithrombotic agent.

The representative embodiment discussed above, wherein the permeable portion is disposed only upon a distal portion of the first balloon and not upon central and proximal portions of the first balloon, and/or wherein the length of the distal portion of the first balloon is less than one half of the length of the first balloon. The permeable portion is disposed around substantially an entire outer circumference of the distal portion of the first balloon.

The representative embodiment discussed above, wherein the catheter is configured to receive an elongate ultrasound probe through the first lumen, with a tip of the probe disposed within the tubular member, wherein the ultrasound energy emitted from the ultrasound probe is focused or reflected by the tubular portion to impart energy to the plurality of microbubbles proximate the first balloon. The ultrasound energy is received and reflected by the plurality of indentations defined upon the outer surface of the tubular portion. The ultrasound probe emits ultrasound energy either substantially perpendicular to a longitudinal axis of the probe or substantially parallel of the longitudinal axis of the probe.

A second representative embodiment of the disclosure provides a method for performing thrombolytic therapy. The method includes the steps of inserting a catheter into and through a patient's vasculature to an area proximate a thrombus, the catheter comprising a distal end portion with an inflatable first balloon defining a first volume therein and comprising a permeable region configured to allow fluid to pass out of the first balloon from the first volume. The catheter further comprises an echogenic tubular portion disposed within the first volume and fixed to a cylindrical wall defining a wire guide lumen, and a proximal end portion defining an inflation lumen providing fluid communication to the first volume. The method further comprises the step of applying a source of fluid to the first volume to expand the first balloon to an expanded configuration and the step of providing a plurality of microbubbles within the first volume that may escape the first volume through the permeable region when the first volume is in the expanded configuration. The method further includes the step of applying a field of ultrasonic energy to the first balloon and the tubular portion disposed therewithin, where the ultrasonic energy field is configured to apply energy to the plurality of microbubbles within the energy field to transfer the plurality of microbubbles to a cavitating state, wherein the tubular portion is configured to reflect or focus the ultrasonic energy received thereon to increase the ultrasonic energy received by the plurality of microbubbles proximate the first balloon.

BRIEF DESCRIPTION OF THE DRAWINGS

FIG. 1 is a partial cross-sectional view of an elongate device for thrombolytic therapy, including a first balloon in a rest configuration.

FIG. 2 is the device of FIG. 1, with the first balloon in an expanded configuration.

DETAILED DESCRIPTION OF THE DRAWINGS AND THE PRESENTLY PREFERRED EMBODIMENTS

Figure 2A:
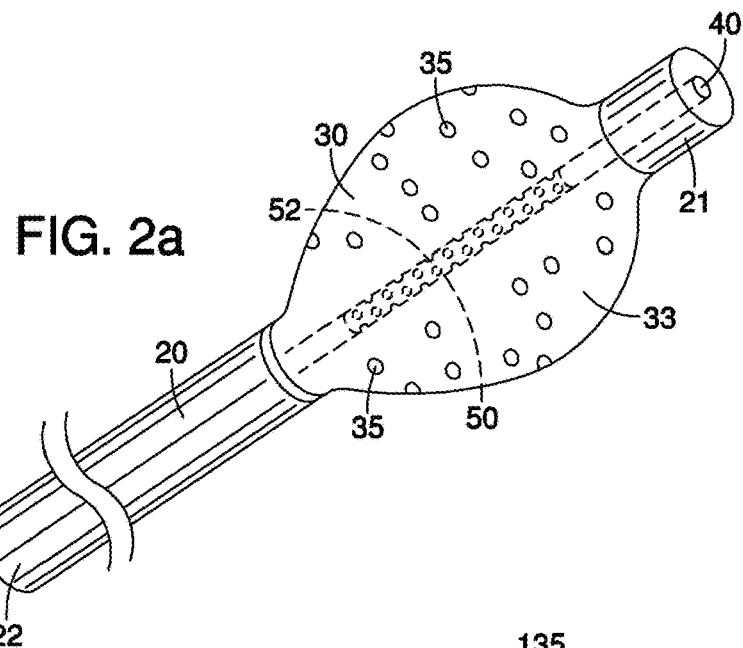
FIG. 2a is a perspective view of the device of FIG. 1, with the first balloon in the expanded configuration.
Figure 2B:
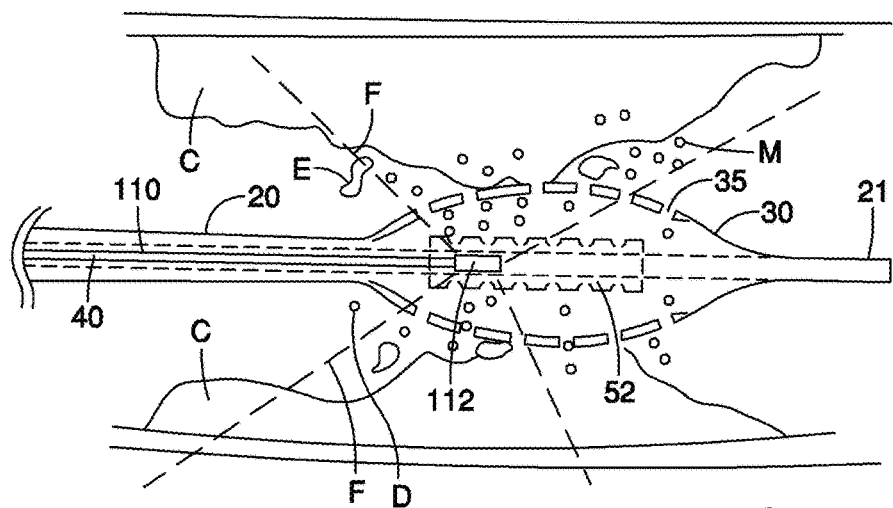
FIG. 2b is a cross-sectional view of the device of FIG. 1 implanted proximate a thrombus within a patient's vasculature.
Figure 2C:
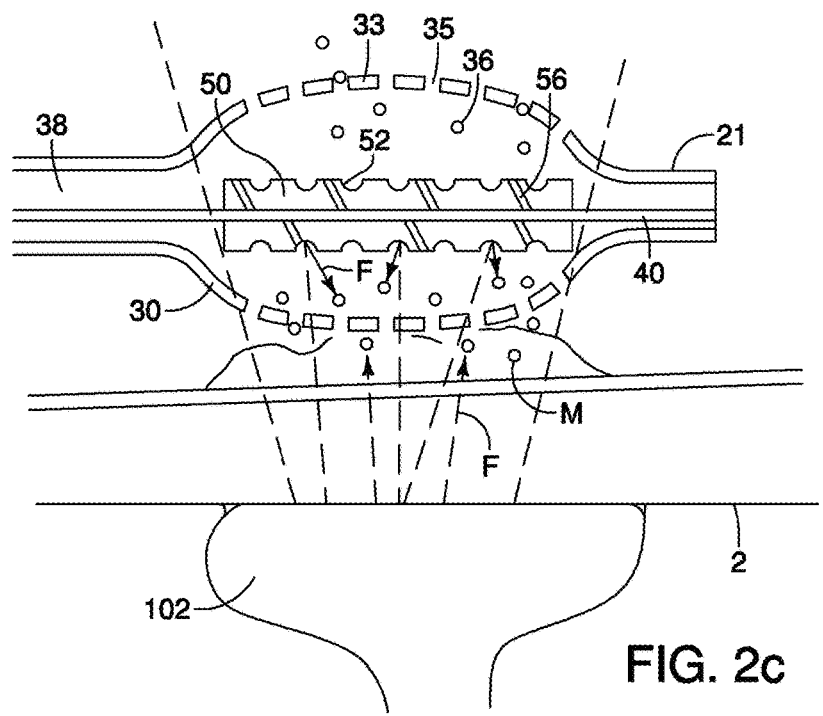
FIG. 2c is a schematic view of the device of FIG. 1 in the expanded position used in conjunction with an external ultrasound source.

Turning now to FIGS. 1-2b, a device 10 for thrombolytic or restenosis therapy is provided. The device 10 includes an elongate catheter 20 with a distal end portion 21, a proximal end portion 22, and a wire guide lumen 40 disposed therethrough. The wire guide lumen 40 supports a tubular portion 50 that is disposed within a volume 36 defined by an inner surface of an expandable balloon 30 disposed upon the distal end portion 21 of the catheter.

The catheter 20 is configured to be of sufficient length for placement within the desired area of the patient's vasculature from various convenient points of percutaneous entry, or to be inserted into the vasculature from a convenient orifice of the patient, such that the distal end portion 21 is disposed proximate to (either extending through or closely abutting) the blood clot and the proximal end portion 22 extends out of the patient for manipulation by the physician. In some embodiments, the catheter 20 may be 80 cm to 180 cm, although shorter or longer catheters 20 may be provided depending on the desired location for use and implantation within the patient. The catheter 20 includes a first balloon 30 that is disposed upon the distal end portion 21 of the catheter 20, preferably very close to the tip of the distal end portion 21. The first balloon 30 may be formed with a variety of lengths as needed for various medical procedures. For example, the first balloon 30 may have a length from about 2 cm to about 40 cm, or any length within this range as needed. The inflated diameter of the first balloon 30 may be from 1 mm to 4 cm as needed for the specific medical procedure, or any inflation diameter within this range. In some embodiments, the volume within the expanded first balloon 30 may be between about 0.5 and about 2.5 cc, inclusive of all volumes within this range. In embodiments shown in FIGS. 1-10, the first balloon may be a compliant balloon, while in other embodiments shown in FIG. 11 the first balloon 30 may be a substantially non-compliant balloon. Unless otherwise noted herein, the structure depicted and discussed with respect to the compliant balloons within this specification are equally applicable in a non-compliant balloon. For the sake of brevity, the same element numbers are used for similar components in the depiction of the non-compliant balloon in FIG. 11 as used in FIGS. 1-2.

The first balloon 30 is sufficiently flexible to expand from a first rest position (FIG. 1) where the walls of the first balloon 30 coaxially surround and is proximate to the wire guide lumen 40 to a second expanded position (FIG. 2) where the central portion of the first balloon 30 expands away from the wire guide lumen 40 in a curved fashion and the proximal and distal ends of the first balloon 30 remain constrained to the catheter 20. The first balloon 30 is formed about the entire periphery of the wire guide lumen 40 and therefore expands radially outward from the wire guide lumen 40 along all sides of the catheter 20.

As shown in FIG. 2b, the catheter 20 may be positioned so that the balloon 30 and tubular portion 50 (discussed below) is positioned within a lumen D defined by the thrombus C. Accordingly, the outward expansion of the balloon 30 may assist in compressing or fragmenting the thrombus C due to the force disposed thereupon by the expanded first balloon 30, with additional assistance of the microbubble flux M directed to the thrombus from the balloon 30 (energized by ultrasound energy F provided by an ultrasound source 112, such as an IVUS source depicted in FIGS. 3b and 3) and with the antithrombotic bioactive agents presented thereto (each discussed below).

As best shown in FIGS. 1-2, the first balloon 30 may be configured with one or more permeable portions 33 that are disposed along the periphery of the first balloon 30. Specifically, the first balloon 30 may include a plurality of apertures, or pores 35 defined through the wall of the first balloon 30 that allow fluid communication from the volume 36 defined between the outer surface of the wire guide lumen 40 (and tubular portion 50, discussed below) and the inner surface of the first balloon 30. The plurality of apertures 35 may be configured within the first balloon 30 to expand in size as the first balloon 30 expands from the rest position to the expanded position by filling the volume 36 with a pressurized fluid or gas. The walls of the first balloon 30 stretch as the volume 36 is expanded, which causes the area of the apertures 35 to similarly increase in size. In some embodiments, the plurality of apertures 35 expand to an area just larger than the diameter of a typical microbubble, such as about 2-3 microns. In other embodiments, the apertures 35 may be sized between approximately 0.1 microns and 500 microns, alternatively between about 0.1 microns and 100 microns, or between about 0.1 microns and 10 microns. These ranges of aperture sizes have been found to be adequate for at least some of the expected or typical antithrombotic drugs to be used with the device 10. For example, a typical antithrombotic drug streptokinase is 47.0 to 50.2 Kd. Streptokinase has 414 Amino acid residues.

Several types of microbubble solutions known in the art may be used to establish the plurality of microbubbles within the internal volume 36 of the first balloon (and similarly used with other embodiments discussed below). For example, suitable bubble contrast or liposome solutions are commonly available that may be suitable for use. One suitable solution is polyethyleneglycol (PEG) modified liposomes solution that contains perfluoropropane. Microbubble solutions may also be created by entraining gas into a solution of sodium chloride or other physiologicmedia. An inert gas such as Argon may be used. Several methods of creating liposomes, micelles or other spherical particles using lipids such as phosphatidylcholine may be used. Similarly proteins such as albumin may be used to create the microbubble shell. In some embodiments microbubble solutions such as Levovist® of Berlex, Canada, and Optison™ of GE Healthcare may be used. Conventional nonionic contrast solutions may be appropriate.

In some embodiments and shown schematically in FIG. 1, a bioactive agent A may be coated onto an inner or an outer surface of the balloon 30, or injected or supplied within the internal volume 35 of the balloon to provide a desired pharmcolegocial or physical effect in conjunction with the patient, such as destruction of a thrombus or removal or shrinkage of restenosis. In an exemplary embodiment, the bioactive agent is an antithrombotic agent. Catheter balloons 30 comprising an antithrombotic agent (either coated thereon, or in solution within the internal volume 35 defined by the balloon 30) are particularly preferred for implantation in areas of the body that contact blood and where a thrombus for removal or destruction has been directly noted by observation or indirectly noted. An antithrombotic agent is any agent that inhibits or prevents thrombus formation within a body vessel, or chemically breaks down a blood clot or thrombus in existence. Types of antithrombotic agents include anticoagulants, antiplatelets, and fibrinolytics. Examples of antithrombotics include but are not limited to anticoagulants such as Factor Xa, Factor Vila and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin. Suitable bioactive agents have been previously disclosed in pending U.S. Published Application No. 2008/0200977 titled "Artificial Valve Prostheses with Free Leaflet Portion," which is commonly assigned with the underlying application, and is hereby fully incorporated by reference herein.

Further examples of potentially suitable antithrombotic agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenala- nyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; as well as endothelial progenitor cells or endothelial cells.

Figure 9:
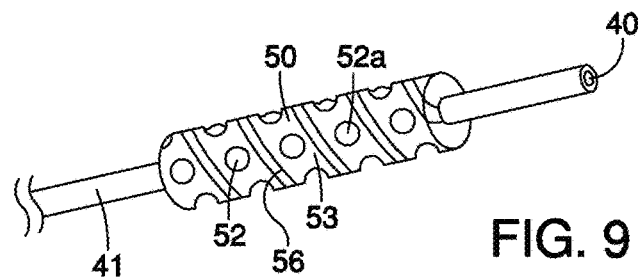
FIG. 9 is a detail view of the tubular portion of the device of FIG. 1.

With combined reference to FIG. 9, the tubular portion 50 is disposed upon a cylindrical wall 41 within the catheter 20 that defines the wire guide lumen 40 and is additionally disposed within the volume 36 defined within and surrounded by the inner surface of the first balloon 30. The tubular portion 50 may be fixed to the wall 41 with adhesive or with a press fit connection, with fasteners, thermally bonded, crimped, or by another method known in the art. The tubular portion 50 is a flexible tubular member that may be formed from various materials, such as metals and various alloys thereof, (Nitinol, stainless steel, titanium, and the like), polymers, composites, and laminates of these various materials. The materials used are preferably echogenic or at least of a greater echogenicity than the materials used to form the catheter 20 and wire guide lumen 40. The tubular portion 50 may be substantially the same length as the first balloon 30 or in some embodiments, the tubular portion 50 may be shorter than the first balloon 30 with the tubular portion 50 centered within the first balloon 30, or otherwise oriented within the volume 36 defined by the first balloon 30. In an exemplary embodiment, the tubular portion may have an outer diameter of approximately 0.040 inches with an inner diameter of approximately 0.019 inches. Other suitable material dimensions may be used that are convenient for use within one or more balloons with a catheter device configured for implantation within the vascular system of a typical patient.

In some embodiments, the tubular portion 50 may include a helical cut 56 defined along the length thereof, which is provided to increase the flexibility of the tubular portion 50 and therefore the distal end portion 21 of the catheter 20. The helical cut 56 may be formed upon the tubular portion 50 with a laser cutter, EDM, or other type of processing apparatus known to provide fine and precise cuts upon a tubular metal member. The helical cut 56 is formed with a pitch sufficient to provide optimal flexibility to the tubular member 50 while not severely affecting the strength in longitudinal tension, or the hoop strength of the tubular portion 50. In some embodiments, the helical cut 56 may have a pitch to make one 360 degree revolution around the tubular portion 50 every 1 mm of length of the portion. In other embodiments, the pitch may be between about 0.5 mm/360 degree revolution and about 2.0 mm/360 degree revolution. A typical thickness of the Nitinol (or other type of suitable material) tubing may be about 0.010 inches, or other suitable thickness for the desired flexibility and strength of the tubular portion 50. Another potential design requirement for the tubing thickness is a wall thickness that allows the desired dimpling 52 (discussed below) without cracking or severely weakening the tubular portion. In some embodiments, the tubular portion may be about 0.670 inches long, while in other embodiments, the tubular portion 50 may be any suitable length based upon the length of the balloon chosen, such as between about 0.5 inches and about 40 inches and any specific desired length within this range. The helical cut 56 is preferably formed through the entire wall thickness of the tubular portion 50, although in some embodiments the helical cut 56 may only extend through a portion of the wall thickness of the tubular portion 50. In still other embodiments, the helical cut 56 may be provided by a weakened region disposed upon the tubular portion 50, such as by periodically providing through cuts (or cuts only partially through the wall thickness) for small distances along the helical pattern, and then neighboring portions where no cuts are made along the helical pattern.

The tubular portion 50 includes a plurality of indentations or dimples 52 that are defined within the surface of the tubular member 50 and extend through a portion of the thickness of the walls of the tubular portion 50. The indentations may be defined in a predetermined pattern upon the surface of the tubular member 50, such as alternating rows of indentations 52 disposed along the length of the tubular member, with the centers 52a of the indentations 52 in one row aligned with the space 53 between neighboring indentations 52 in the two neighboring rows. Other patterns of indentations 52 may be provided. In an exemplary embodiment, a tubular portion may include dimples of about 0.07 mm in diameter, with a spacing of about 0.234 mm between neighboring dimples 52. The dimples 52 are formed with a substantially conical profile at an arc of about 30 degrees. Other types of dimples 52 are contemplated such as pyramidal, semispherical, hemispherical, frustoconical, and the like. The preferred number and spacing of dimples 52 may be a factor of the morphology of the anatomical structure and thrombus (or other type of structure) to be treated by the device 10.

The plurality of indentations 52 are disposed upon the outer surface of the tubular portion 50 to aid in the reflection of incident ultrasonic energy supplied thereto to the region of the patent's vasculature that receives the ultrasonic energy. The indentations 52 also aid in focusing incident ultrasonic energy to the desired region. The placement of indentations at specific locations and with specific geometries also has been determined to focus the incident and reflected ultrasonic energy to a specific distance away from the tubular portion, such as a distance just outside the surface of the balloon where microbubbles M exit the balloon 30 and contact the thrombus proximate to the balloon 30. It has been experimentally determined that microbubbles M that receive ultrasound energy from external sources enter into cavitation, either stable cavitation with continuous application of ultrasound energy, or temporary cavitation until the microbubble bursts. Generally ultrasound devices with standard transducers that operate in the range of 2 to 12 MHz are suitable. Microbubbles that are cavitating have been found to be increasingly effective at destroying the fibrin web of a thrombus over microbubbles that are not cavitating, thus interrupting the physical structure of the thrombus and allowing access for the antithrombotic agent to act upon the thrombus. As discussed above, microbubbles are of a small enough size (nominally about one to two microns) to enter the interior of the thrombus and the fibrin web and locally dissolve the fibrin web, which assists in the degradation of the thrombus.

Figure 10A:
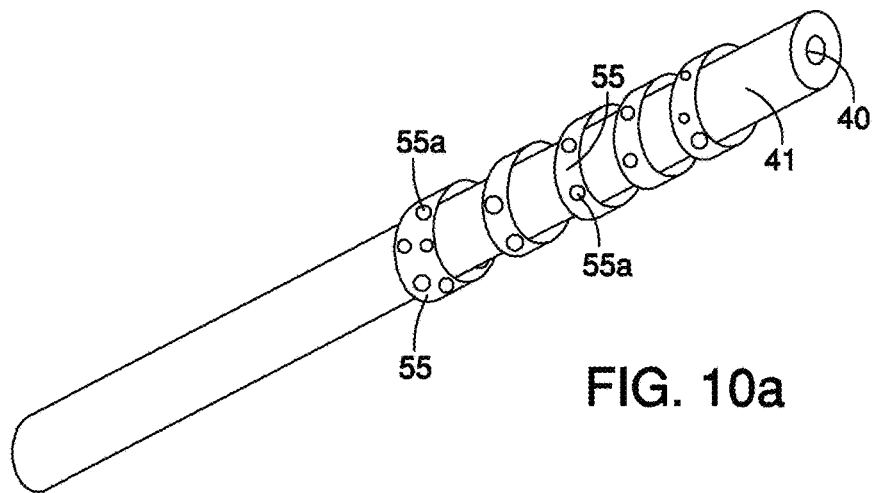
FIG. 10a is a detail view of an alternate echogenic portion usable with the embodiments depicted herein.
Figure 10B:
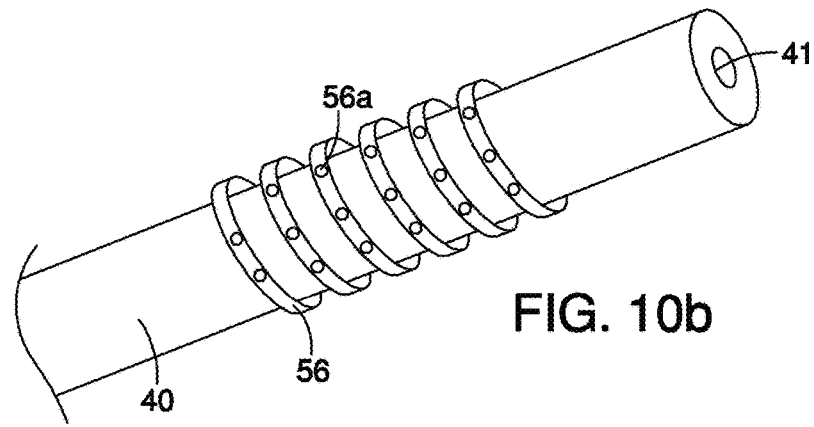
FIG. 10b is a detail view of another alternate echogenic portion.
Figure 11:
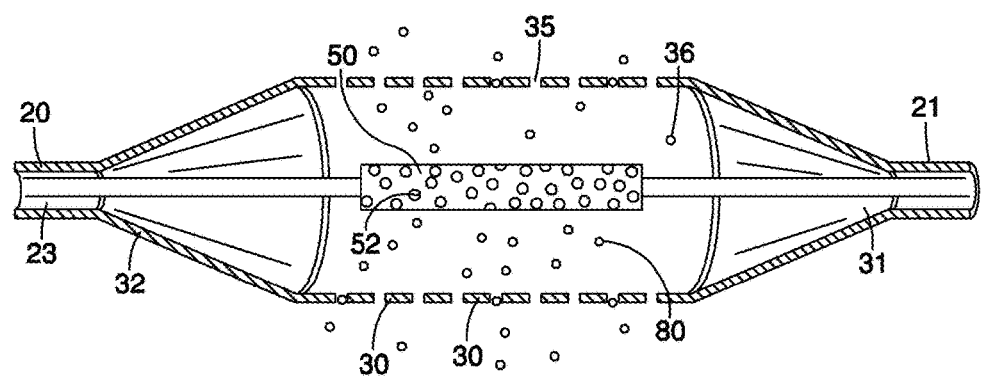
FIG. 11 is a partial cross-sectional view of an elongate device for thrombolytic therapy, with the first balloon being a non-compliant balloon oriented in an expanded configuration.

In other embodiments, an echogenic band may be provided upon the wall 41 of the wire guide lumen 40 that is other than the tubular portion 50, but retains the echoghenic material as well as the plurality of indentations disposed thereon. For example, as shown in FIG. 10a, the echogenic band may be formed with a plurality of segmented bands 55 with indentations thereon 55a. Alternatively, the echoghenic band may formed by an elongate band 56 with indentations 56a that is helically wrapped around the wire guide lumen 40 wall 41.

With continued exposure to microbubbles, preferably energized by incident ultrasound energy, the thrombus is systematically degraded or dissolved to provide increased blood flow through the localized portion of the vasculature due to the removal of the localized head loss. The combination of the compression placed onto the thrombus by the expanded walls of the balloon as well as other practices of mechanical debulking of the thrombus, and the cavitating microbubbles entering into the thrombus causes the thrombus to degrade and reestablishes suitable blood flow through the lumen and the localized application of antithrombotic bioactive agents thereto. Further, the reduction in size of the thrombus additionally reduces the likelihood that a relatively large chunk could break off and eventually flow to the heart and lungs. In some embodiments, a suitable filter or basket, such as the Günther Tulip™ Vena Cava Filter, sold by Cook Medical, may be used in conjunction with, or attached to the device 10 to prevent migration of any chunks or fragments of the thrombus from traveling away from the site in an unintended direction during or following the procedure. In some embodiments, the filter or basket may be configured to be within the same component of the device.

Figure 3:
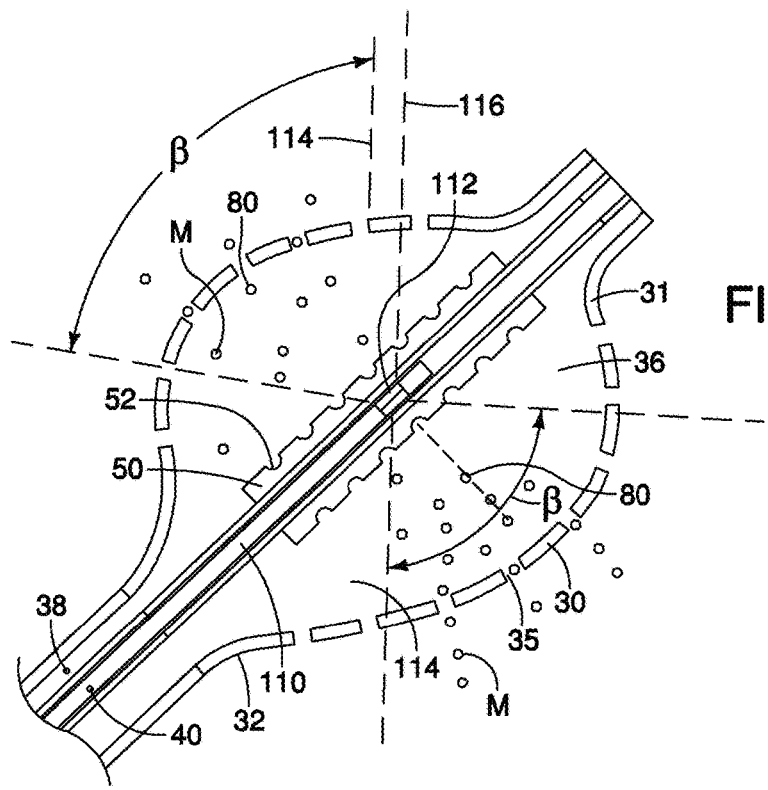
FIG. 3 is the device of FIG. 2, with an ultrasound source disposed within a lumen of the device.

In some embodiments, a source of ultrasonic energy may be used in conjunction with the device 10 to emit a field F of ultrasonic energy to the volume proximate and including the balloon 30 and the thrombus acted upon by the microbubbles. Specifically, as shown schematically in FIG. 2c, an external ultrasound source 102 may be used to direct to and placed against the patient's skin or other outer tissue 2 to direct ultrasound energy to the microbubbles leaving the balloon 30 and reflected and focused by the tubular portion 50 and specifically by the indentations 52 upon the tubular portion 50. Alternatively, as shown in FIGS. 2b and 3, an intravascular ultrasound device (IVUS) 110 may be threaded through the wire guide lumen 40 of the catheter 20 to be disposed proximate and in some embodiments within the lumen of the tubular portion 50. The IVUS device may emit ultrasonic energy radially away from the probe 112 of the device in a conical pattern relatively perpendicular to the elongate probe 112, while in other embodiments, the IVUS probe 112 may emit ultrasound energy conically in substantially in a direction parallel to the length of the probe 112. The ultrasound device (external or IVUS) may also be used to assist in placing the catheter, by viewing the echogenic tubular portion 50 proximate to the location of the thrombus.

Figure 4A:
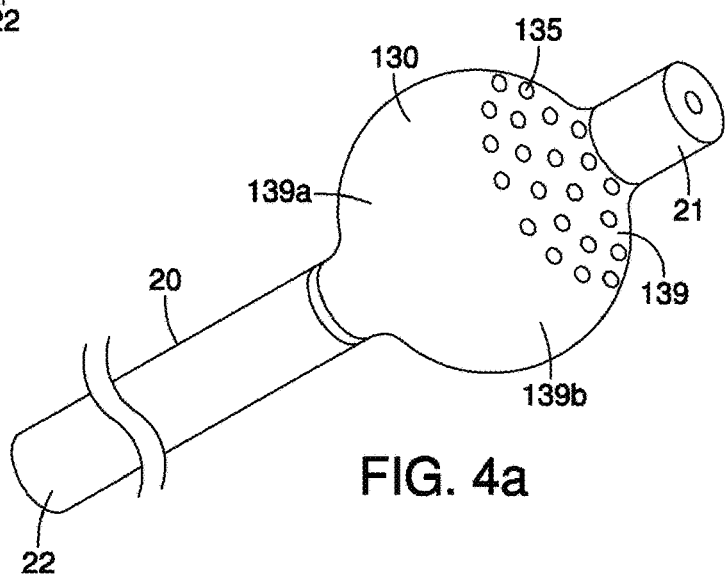
FIG. 4a is a perspective view of the device of FIG. 4.
Figure 4B:
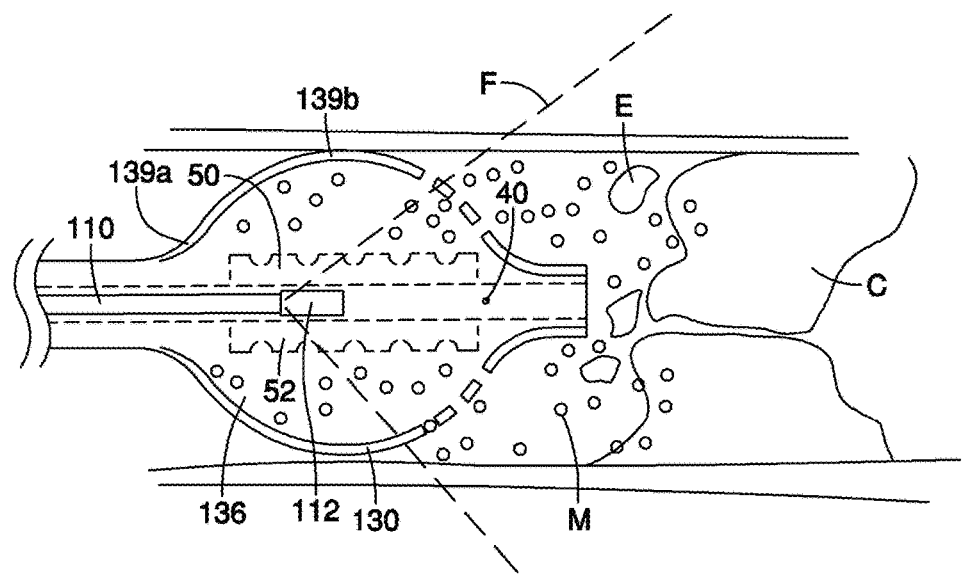
FIG. 4b is a cross-sectional view of the device of FIG. 4 implanted proximate a thrombus within a patient's vasculature.
Figure 4C:
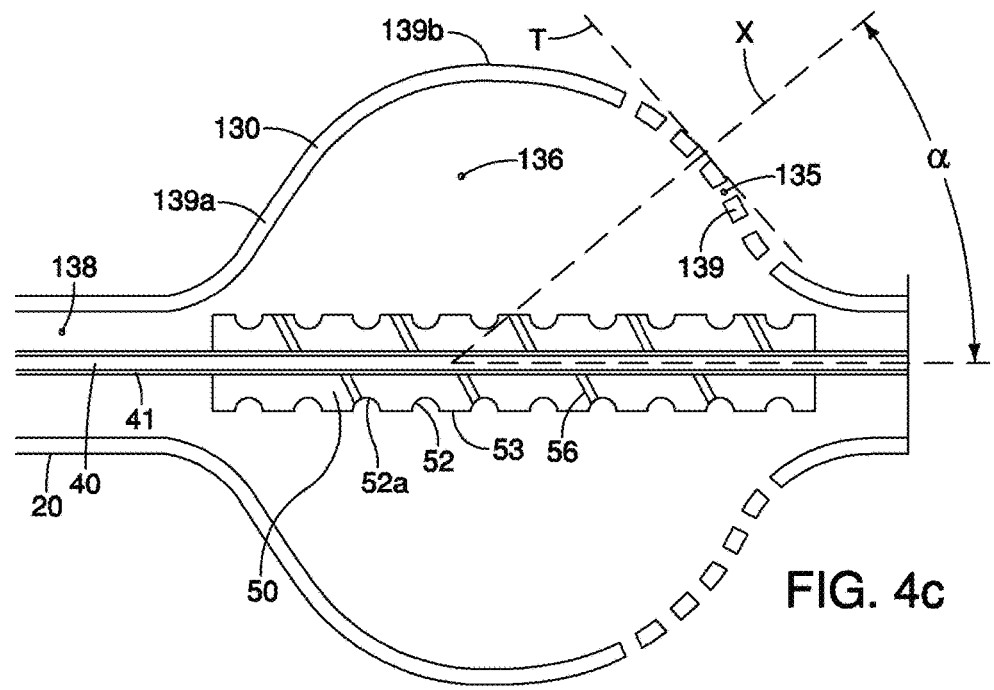
FIG. 4c is a detail view of the device of FIG. 4.
Figure 4:
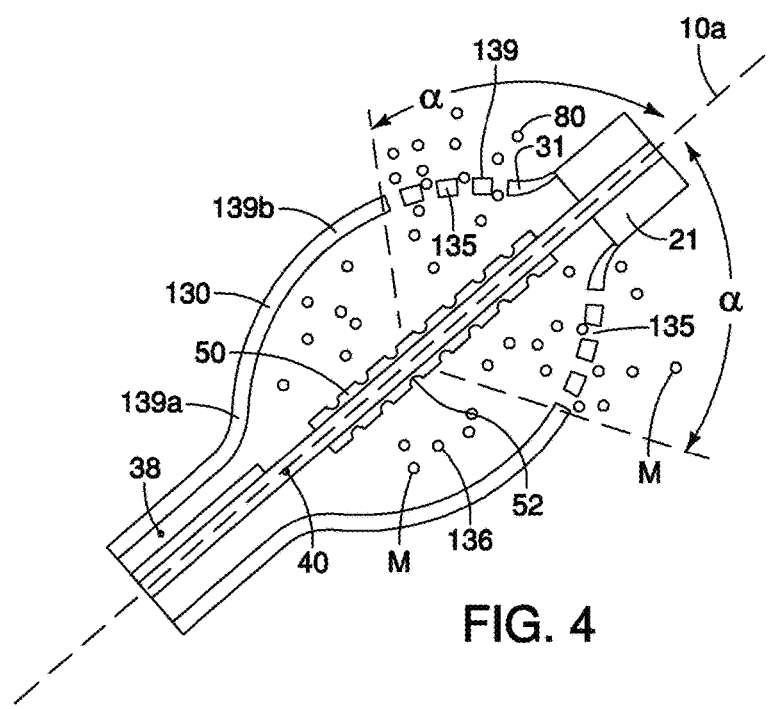
FIG. 4 another elongate device for thrombolytic therapy with the balloon in the expanded configuration.

Turning now to another representative embodiment depicted in FIGS. 4 and 4a, the medical device 100 includes a catheter 20 formed similarly to the embodiment of FIGS. 1-2 discussed above. For the sake of brevity like components are referenced with like element numbers herein. The catheter includes a first balloon 130 inflatably disposed upon the distal end portion 21 of the catheter 20, and may be selectively inflated by applying a pressurized liquid or gas into the internal volume 136 defined between the inner surface of the balloon 130 and the outer surface of the wire guide lumen 40 and the tubular portion 50, as discussed above. The first balloon 130 may include a coating a bioactive agent (such as coating A shown schematically in FIG. 1) on either the inner or outer surface, or may be preloaded with or receive a bioactive agent within the inner volume 136 of the balloon. The bioactive agent may be an antithrombotic agent. Suitable antithrombotic agents are discussed in the embodiments above. The antithrombotic agent is configured to be releasable from the first balloon 130 (when coated thereon) or pas through the permeable region 133 when the balloon 130 is in the expanded configuration.

The first balloon 130 may include a permeable distal portion 139 defined by a plurality of apertures 135 configured to allow microbubbles and bioactive agents (when provided) to pass through, and a proximal portion 139a (and in some embodiments a central portion 139b) that is not permeable to microbubbles and bioactive agents. The permeable distal portion 139 of the first balloon 130 may include a plurality of apertures 135 disposed therein, about the substantially entire circumference of the distal portion 139 of the first balloon 130, which allows microbubbles and bioactive agents to flow from the internal volume 136 of the balloon, and enter and react with a thrombus disposed within the lumen of a patient's vasculature and proximate the balloon 130. A schematic view of the operation of the first balloon 130 and catheter 20 proximate a thrombus C is provided in FIG. 4b. As shown in FIG. 4c, the apertures 135 are defined from the distal end 131 of the balloon 130 and extend along a portion 139 of the balloon 130, such that the apertures 135 formed in the permeable portion are disposed within a surface of the balloon 130 defined by angle α, defined by a line X perpendicular to a tangent line T upon the outer surface of the balloon 130 at the aperture 135 and the longitudinal axis of the tubular portion 50. In some embodiments, the angle α may be about 45 degrees, about 30 degrees or within the range of about 15 degrees to about 90 degrees, inclusive of angles within this range, would be suitable.

In other embodiments, the length of the permeable portion 139 may be less than half of the length of the balloon 130, measured from the distal end 131 of the balloon 130. In other embodiments, the length of the permeable distal portion 139 may be less than one quarter of the length of the balloon. In still other embodiments, the permeable distal portion 139 may be configured such that the apertures disposed upon the balloon 130 are positioned distally of the circumferential portion 139c (FIG. 4b) that extends radially the furthest away from the tubular portion 50. As can be understood with reference to FIG. 4b, this configuration of the permeable distal portion 139 substantially prevents microbubbles M and bioactive agent emitted from the permeable portion 139 from flowing toward the proximal end portion 22 of the catheter 20, when the balloon 130 fully occludes the lumen defined with the vasculature. This configuration has the benefit of preventing unwanted backflow of microbubbles, bioactive agents, or other solution away from the thrombus being treated, which could have unwanted effects during the procedure.

Providing the plurality of apertures 135 only within the front portion 39 of the balloon 130 further allows the microbubbles produced within the internal volume 136 of the balloon 130 to escape from only the forward portion of the balloon 30 and enter and concentrate upon an occlusion or thrombus that is disposed directly ahead of and proximate to the distal end of the catheter 20. Concentrating the escaping microbubbles within only the front portion 139 of the balloon is theorized to increase the concentration of microbubbles that enter the volume of the thrombus proximate to the balloon 130 and therefore increase the effectiveness of the destruction of the fibrin web by the cavitating microbubbles (based on the incident ultrasound energy provided by the ultrasound source, discussed above). Similarly, the balloon 130 with forwardly disposed apertures 135 is suitable for directing microbubbles that escape through the apertures 135 toward a thrombus that covers the majority of or all of the cross-sectional area of the vein, artery, or capillary, when it is difficult or impossible to extend the distal end portion 21 of the catheter 20 through the thrombus to align the balloon 130 therewith. As can be understood with reference to FIG. 4b the forward firing balloon 130 imparts microbubbles upon the exposed outer surfaces of the thrombus, and continued application of microbubbles and ultrasound energy (as focused and increased by the tubular portion 50) allows the device to "drill" through the thrombus to form and/or increase the diameter of the lumen within the path available for blood flow. Additionally, the application of the microbubbles and ultrasound energy upon an outer side surface of the thrombus, in combination with the expansion of the balloon 130 to the vessel wall substantially occludes flow past the balloon 130 toward the proximal portion of the catheter 20 and thrombus particles E that are removed from or fall off of the thrombus C are maintained between the balloon 130 and the larger thrombus C. Accordingly, the "floating" particles remain within the microbubble-rich blood solution and within the flux of ultrasound energy (and in some embodiments in the solution with relatively high concentrations of antithrombotic bioactive agents) to aid in their destruction. Accordingly, the particles removed from the thrombus are smaller when the procedure is concluded and therefore less of a risk to cause damage if they migrate through the patient's bloodstream and into the patient's heart and/or lungs.

As discussed further herein, an IVUS (intravascular ultrasound) device 110 (shown schematically in FIGS. 3 and 4b) that emits ultrasound energy from the forward end portion 112 thereof and in a direction generally in a forward direction away from the IVUS device may be threaded through the wire guide lumen 40 of the device 10, and emit ultrasound toward the distal end 21 of the catheter 20 and therefore within the space between the balloon 130 and the thrombus and additionally into the volume of the thrombus, which may include microbubbles that have entered the internal volume of the thrombus. A preferred forward firing IVUS 110 device would emit a cone of ultrasound energy F that leaves the device at approximately the angle α to maximize the efficiency of the application of ultrasound energy to the microbubbles within or proximate the edge of the thrombus.

The size and alignment of the dimples 52 are configured to maximize the reflection of ultrasonic energy applied to the tubular portion 50, from an ultrasound source external to the patient applied and focused onto the volume surrounding the catheter balloon and thrombus, or an IVUS device (either side firing or forward firing) that is threaded through the wire guide lumen 40 of the catheter 20 after the catheter is positioned within the patient (either extending through the thrombus or proximate an end of a thrombus.

Figure 5:
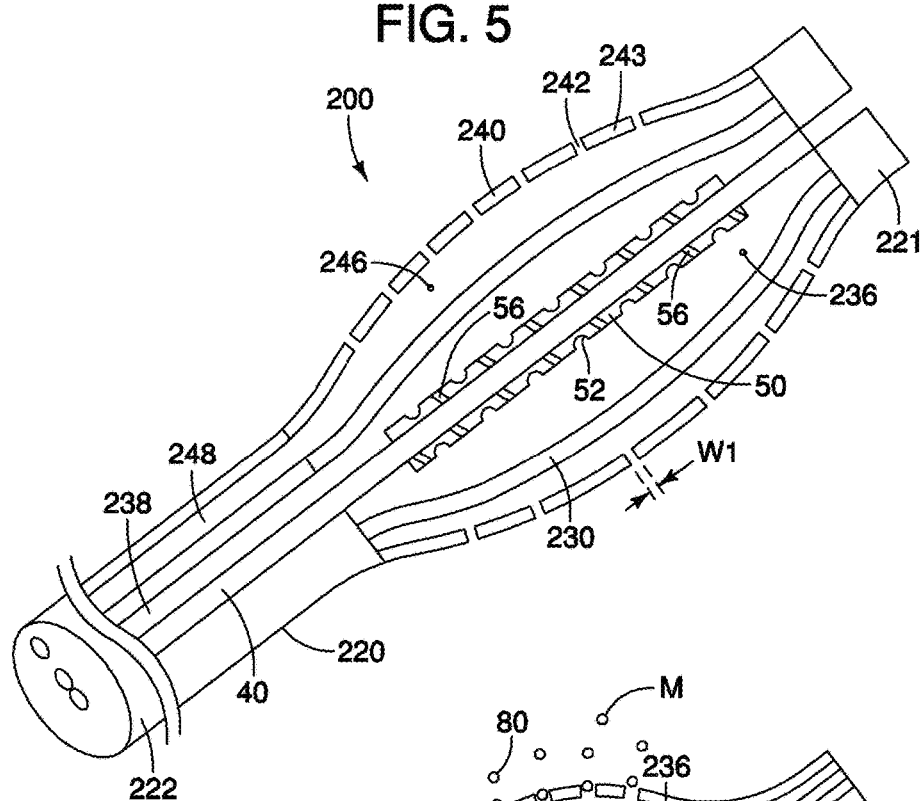
FIG. 5 is yet another elongate device for thrombolytic therapy with first and second balloons in a rest configuration.
Figure 6:
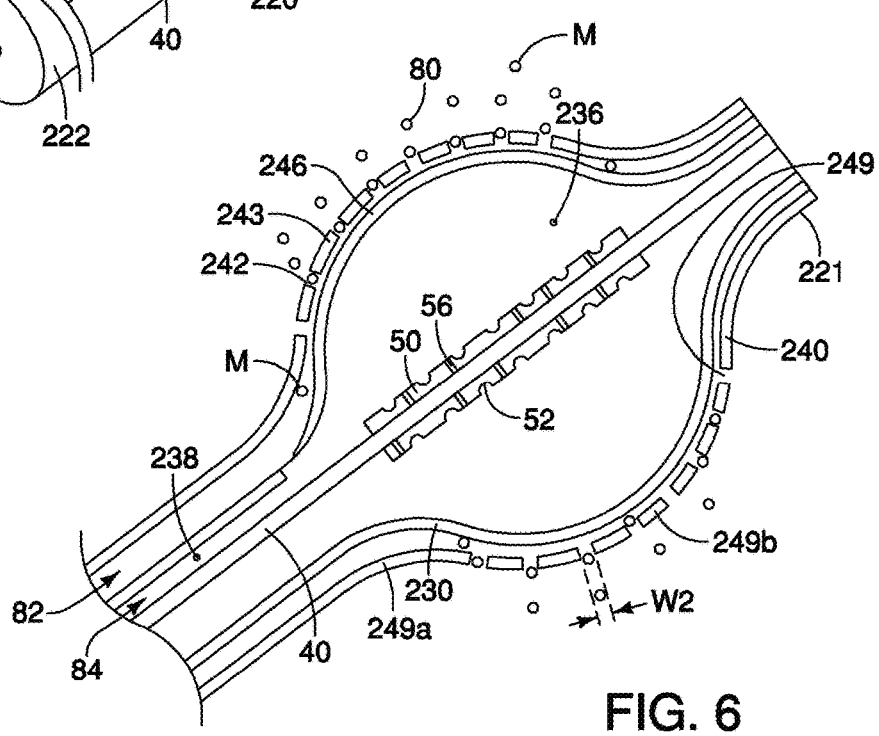
FIG. 6 is the device of FIG. 5 showing the first and second balloons in an expanded configuration.

Turning now to FIGS. 5-6, another representative embodiment of the disclosure is provided and depicts a medical device 200. The medical device 200 is formed with many of the structural features present in medical device 10, and therefore for the sake of brevity similar features between these embodiments are referenced herein with the same element numbers. The medical device 200 includes an elongate catheter 220 with first and second end portions 221, 222. The elongate catheter may include multiple lumens defined through all or portion of the length of the catheter 220. A guide wire lumen 40 is disposed through the entire length of the catheter 220 and includes apertures at the distal and proximal end faces to receive a guide wire or other thin elongate structure therethrough and allow the elongate structure to pass through the entire length of the catheter 220. The device 200 includes a tubular portion 50 that is coaxially fixed to the wire guide lumen 40 and disposed within the distal end portion 221 of the catheter 220. The tubular portion 50 includes a plurality of indentations 52 disposed about the outer surface thereof, and may include a helical cut 56 that extends along the length of the tubular portion 50. The indentations 52 and the helical cut 56 may be disposed upon the tubular portion 50 as discussed in the embodiments discussed elsewhere herein.

Figure 12:
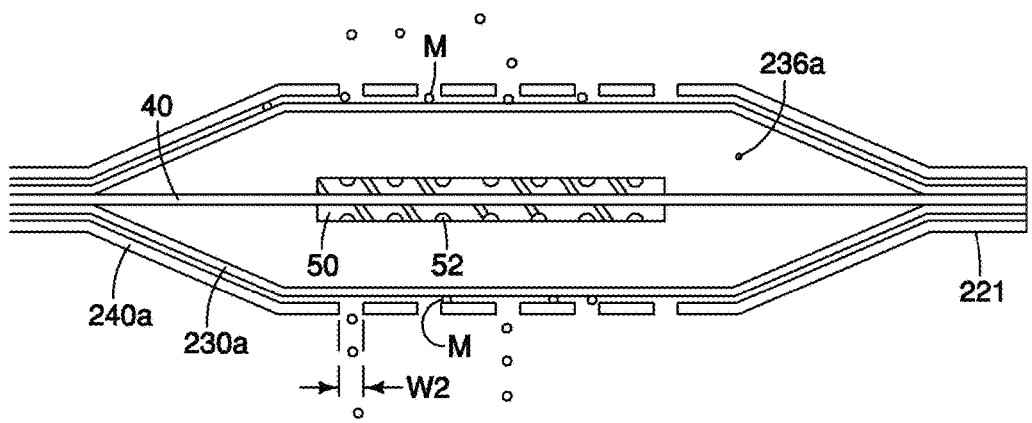
FIG. 12 is the view of FIG. 6, wherein the first and second balloons are non-compliant balloons.

The catheter 220 includes an inner first balloon 230 and an outer second balloon 240. Each of the first and second balloons 230, 240 are disposed upon the distal end portion 221 of the catheter, surrounding and coaxial with the tubular portion 50. The first balloon 230 is configured to be expandable between a first rest position (FIG. 5) where the walls of the first balloon 230 are substantially parallel with the length of the tubular portion 50 to a second expanded position (FIG. 6) where the central portion of the first balloon 230 expands away from the wire guide lumen 40 in a curved fashion, with the distal and proximal ends of the first balloon 230 constrained by the catheter 220. In other embodiments where at least the second balloon 240*a* (and potentially the first balloon 230*a*) is/are non-complaint balloons, as shown in FIG. 12, the central portion of the first balloon extends away from the guide wire lumen 40 to an expanded position wherein the balloon expands such that the surface of the balloon remains substantially parallel to the guide wire lumen. The first balloon 230 is formed about the entire periphery of the catheter 220 and therefore expands radially outward from the wire guide lumen 40 along all sides of the catheter 220. The internal volume 236 of the first balloon 230 is defined between the inner surface of the first balloon 230 and the outer surface of the cylindrical wall 41 defining the wire guide lumen 40 and the tubular portion 50, and is in fluid communication with the end of the proximal portion 222 of the catheter 220 through the first lumen 238. The first lumen 238 may be configured with a luer lock adaptor or similar structure to mechanically and fluidly accept a source of fluid or gas thereon and allow fluid or gas pumped into the first lumen 238 to flow into the cavity 236 and thereby expand the first balloon to the expanded position.

The porous second balloon 240 is disposed coaxially about the outer surface of the first balloon 230 and is constrained to the catheter 220 at both the distal and proximal ends of the second balloon 240. As discussed above, the second balloon 240*a* may be a non-compliant balloon as depicted in FIG. 12. The second balloon is expandable between a rest position (FIG. 5) where the second balloon 240 is substantially parallel with the tubular portion 50 and the outer diameter of the second balloon 240 is substantially the same as the outer diameter of the remaining portions of the catheter 220, and an expanded configuration (FIG. 6, with an outer construction similar to that depicted in FIG. 2*a* of the embodiment device 10 discussed above) where the second balloon 240 is expanded outward with the central portion 249*b* of the second balloon 240 being radially outward from the tubular portion with the distal and proximal ends 249, 249*a* of the second balloon 240 remaining constrained by the catheter 20 walls.

In some embodiments, the second balloon 240 may be coated (either upon the inner or outer surface thereof) with a bioactive agent, such as an antithrombotic agent, as discussed in the embodiments presented above. A schematic example of the coating upon the second balloon 240 may be understood with reference to the coating A upon the balloon 30, shown in FIG. 1.

In some embodiments, the second balloon 240 is expanded outward to the second position due outward expansion force applied thereto by the outer surface of the first balloon 230 as it expands to the expanded position upon the receipt of pressurized fluid or gas within the volume 236 of the first balloon 230. In this configuration, the outer geometry of the second balloon 240 substantially matches and surrounds the outer geometry of the first balloon 230, with the walls of the second balloon being positioned outside of the first balloon 230.

In some embodiments, the volume 246 defined between the inner surface of the second balloon 240 and the outer surface of the first balloon 230 may be in fluid communication with the outside of the catheter 220 through a second lumen 248 that is defined within the catheter 220 and extends to an aperture or port located at the proximal end of the proximal portion 222 of the catheter 220. The second lumen 248 may serve many purposes, such as allowing microbubble solution to be injected into the second lumen 248 and therefore the second volume 246 (either prior, during, or after expansion of the first balloon 230) or allowing bioactive agents (such as antithrombotic bioactive agents, as discussed above) to be pumped into the second volume 246, either in conjunction with pumping the microbubble solution or independently of the microbubble solution. In some embodiments, the second lumen 248 may be fluidly connected with one or more luer adapters or similar structures to mechanically and fluidly receive a fluid or gas source thereupon. In embodiments where it is desired to add bioactive agents to the second volume 246 separately from microbubble solution, two independent luer adaptors (or the like) are fluidly and mechanically connected with the second lumen 248.

The second balloon 240 may include a permeable region 243 defined by a plurality of apertures 242 that are disposed around substantially the entire circumference of the balloon 240, which allow selective fluid communication from within the volume 246 of the second balloon 240 to the volume surrounding and outside of the second balloon 240. In some embodiments, the porous second balloon is configured such that the size of the apertures 242 increase as the second balloon 240 expands (either due to the expansion of the inner, first balloon 230 and/or due to fluid or gas being pumped into the second volume 246 through the second lumen 248). As the size of the plurality of apertures 242 increase, and the pressure within the second volume 246 similarly increases, fluid within the second volume 246 is urged out of the second volume 246 due to the differential pressure between the second volume 246 and the environment surrounding the outer surface of the second balloon.

In some embodiments, the apertures 242 are sized to allow microbubbles present within the second volume 246 to flow through the apertures 242 when the second balloon 240 is in the expanded configuration, but prevent a significant amount of other fluid to escape the second volume 246 therethrough. Suitable sizes for the plurality of apertures 242 are discussed with respect to apertures 35 in embodiments above. In some embodiments, the apertures 242 may be sized to allow bioactive agents (as discussed above) to flow through when the second balloon 240 is in the expanded configuration, to allow both microbubbles and the bioactive agents in solution to act upon the thrombus disposed proximate to the balloon 240.

Figure 8:
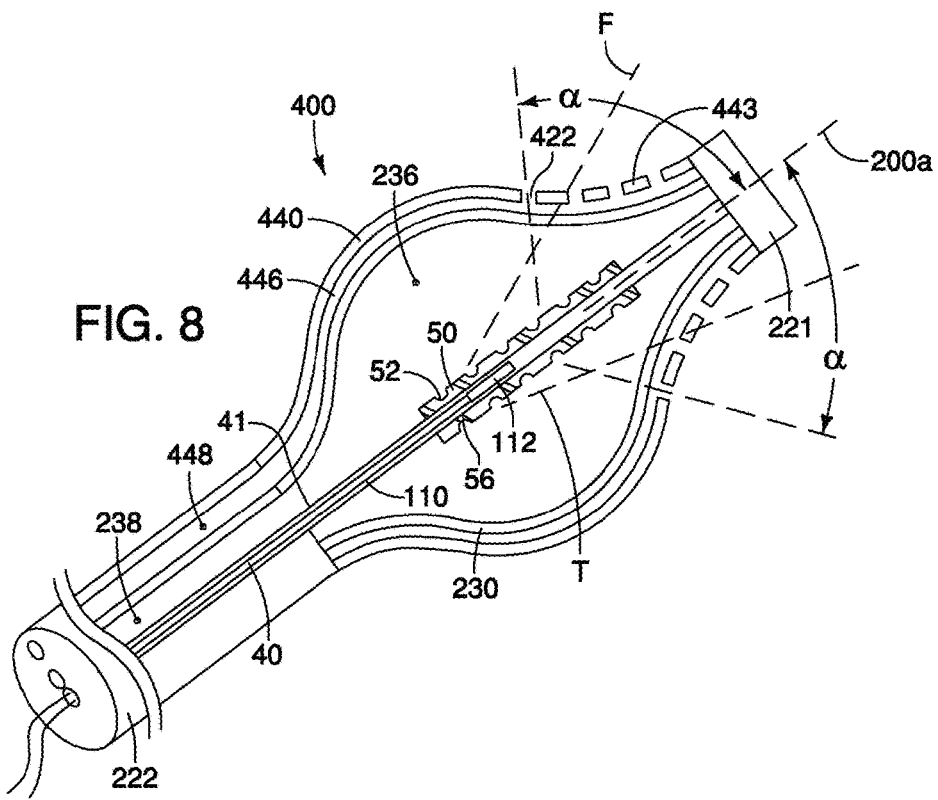
FIG. 8 is the device of FIG. 7 with the first and second balloons in an expanded position.
Figure 7:
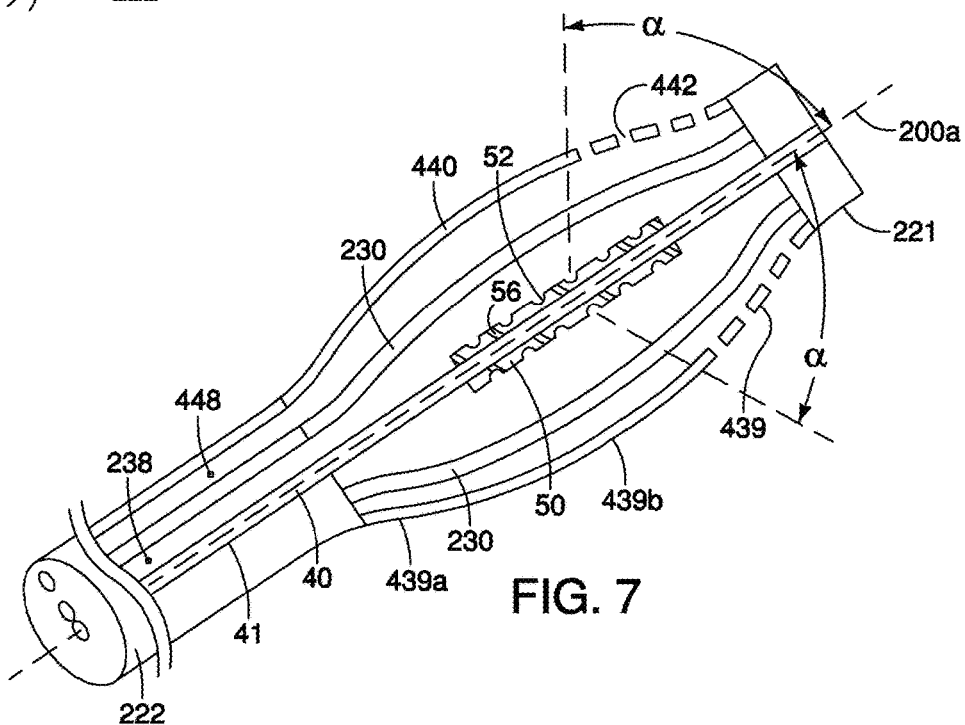
FIG. 7 is yet another elongate device for thrombolytic therapy with first and second balloons in a rest position.

Turning now to FIGS. 7-8, another representative device 400 thrombolytic or restenosis therapy is provided. The device 400 includes many structures similar to like structures discussed elsewhere in this specification and drawings and, for the sake of brevity, like structures will be designated with like element numbers. The device 400 includes an elongate catheter 220 with first and second end portions 221, 222. The elongate catheter may include multiple lumens defined through all or portion of the length of the catheter 220. A guide wire lumen 40 is disposed through the entire length of the catheter 220 and includes apertures at the distal and proximal end faces to receive a guide wire or other thin elongate structure therethrough and allow the elongate structure to pass through the entire length of the catheter 220. The device 400 includes a tubular portion 50 that is coaxially fixed to the wire guide lumen 40 and disposed within the distal end portion 221 of the catheter 220. The tubular portion 50 includes a plurality of indentations 52 disposed about the outer surface thereof, and may include a helical cut 56 that extends along the length of the tubular portion 50. The indentations 52 and the helical cut 56 may be disposed upon the tubular portion 50 as discussed in the embodiments discussed elsewhere herein.

The catheter 220 includes an inner first balloon 230 and an outer second balloon 440. Each of the first and second balloons 230, 440 are disposed upon the distal end portion 221 of the catheter, surrounding and coaxial with the tubular portion 50. The first balloon 230 is configured to be expandable between a first rest position (FIG. 7) where the walls of the first balloon 230 are substantially parallel with the length of the tubular portion 50 to a second expanded position (FIG. 8) where the central portion of the first balloon 230 expands away from the wire guide lumen 40 in a curved fashion, with the distal and proximal ends of the first balloon 230 constrained by the catheter 220. The first balloon 230 is formed about the entire periphery of the catheter 220 and therefore expands radially outward from the wire guide lumen 40 along all sides of the catheter 220. The internal volume 236 of the first balloon 230 is defined between the inner surface of the first balloon 230 and the outer surface of the cylindrical wall 41 defining the wire guide lumen 40 and the tubular portion 50, and is in fluid communication with the end of the proximal portion 222 of the catheter 220 through the first lumen 238. The first lumen 238 may be configured with a luer lock adaptor or similar structure to mechanically and fluidly accept a source of fluid or gas thereon and allow fluid or gas pumped into the first lumen 238 to flow into the volume 236 and thereby expand the first balloon 236 to the expanded position.

The second balloon 440 is disposed coaxially about the outer surface of the first balloon 230 and is constrained to the catheter 220 at both the distal and proximal ends of the second balloon 440. The second balloon 440 is expandable between a rest position (FIG. 7) where the second balloon 440 is substantially parallel with the tubular portion 50 and the outer diameter of the second balloon 440 is substantially the same as the outer diameter of the remaining portions of the catheter 220, and an expanded configuration (FIG. 8, with an outer construction similar to that depicted in FIG. 4a of the embodiment device 100 discussed above) where the second balloon 440 is expanded outward with the central portion 449b of the second balloon 240 being radially outward from the tubular portion with the distal and proximal ends 449, 449a of the second balloon 440 remaining constrained by the catheter 20 walls.

In some embodiments, the second balloon 440 may be coated (either upon the inner or outer surface thereof) with a bioactive agent, such as an antithrombotic agent, as discussed in the embodiments presented above. A schematic example of the coating upon the second balloon 440 may be understood with reference to the coating A upon the balloon 30, shown in FIG. 1.

In some embodiments, the second balloon 440 is expanded outward to the second position due outward expansion force applied thereto by the outer surface of the first balloon 230 as it expands to the expanded position upon the receipt of pressurized fluid or gas within the volume 236 of the first balloon 230. In this configuration, the outer geometry of the second balloon 440 substantially matches and surrounds the outer geometry of the first balloon 430, with the walls of the second balloon being positioned outside of the first balloon 230.

In some embodiments, the volume 446 defined between the inner surface of the second balloon 440 and the outer surface of the first balloon 230 may be in fluid communication with the outside of the catheter 220 through a second lumen 448 that is defined within the catheter 220 and extends to an aperture or port located at the proximal end of the proximal portion 222 of the catheter 220. The second lumen 448 may serve many purposes, such as allowing microbubble solution to be injected into the second lumen 448 and therefore the second volume 446 (either prior, during, or after expansion of the first balloon 230) or allowing bioactive agents (such as antithrombotic bioactive agents, as discussed above) to be pumped into the second volume 446, either in conjunction with pumping the microbubble solution or independently of the microbubble solution. In some embodiments, the second lumen 448 may be fluidly connected with one or more luer adapters or similar structures to mechanically and fluidly receive a fluid or gas source thereupon. In embodiments where it is desired to add bioactive agents to the second volume 446 separately from microbubble solution, two independent luer adaptors (or the like) are fluidly and mechanically connected with the second lumen 448.

The second balloon 440 may include a permeable distal portion 449 defined by a plurality of apertures 445 configured to allow microbubbles and bioactive agents (when provided) to pass through, and a proximal portion 449a (and in some embodiments a central portion 449b) that is not permeable to microbubbles and bioactive agents. The permeable distal portion 449 may be similar to the permeable distal portion 139 discussed above and shown in FIGS. 4, 4a, and 4b. Specifically, the permeable distal portion 449 allows microbubbles (and bioactive agents, when provided within the internal volume 436 of the second balloon 440) to escape only from the distal end portion 449 of the balloon, which has many effects, such as concentrating the microbubble and bioactive agent blood solution proximate the walls of outer walls of the thrombus, and occluding flow past the balloon 440 (when expanded to the proximate the walls of the vasculature lumen) to prevent microbubbles, bioactive agent, or thrombus particles from flowing toward the distal portion of the catheter.

The various described devices (10, 100, 200, 400) described herein may be used to destroy or attenuate vascular thrombi in the following manner. For example, the catheter 10 is inserted into vasculature of a patient, either human or mammal, at a location proximate to the thrombus that has been identified within the patient, either directly or indirectly. The catheter may be inserted percuateously, or through a convenient bodily orifice. The catheter may be threaded into position by extending along a previously placed guidewire positioned through the guide wire lumen 40 that extends along the length of the catheter 20, the guide wire having been previously threaded into position and may be guided into position using a guiding catheter or under the aid of ultrasound.

When positioned proximate to the thrombus to be removed or reduced, the guidewire may be removed from the guide wire lumen 40 and the patient, and the balloon 30 may be transferred to the expanded position by pumping fluid through the first lumen 38 and into the internal volume 36. As the balloon 30 expands to the expanded position due to the increased fluid pressure within the internal volume, the plurality of apertures 35 defining the permeable region 33 expand with the expansion of the balloon 30. While fluid is pumped into the internal volume, microbubble solution (as discussed in detail above) is additionally pumped into the internal volume 36 either mixed with the fluid that was initially used to expand the balloon 35 or as a separate step after the balloon 35 is expanded. The microbubbles within the internal volume are small enough such that the microbubbles proximate the apertures 35 flow through the permeable portion 33 and out of the balloon 30. In embodiments where a bioactive agent, such as an antithrombotic agent (as discussed above) is provided, the bioactive agent may either simultaneously or sequentially be pumped into the internal volume 36, with the fluid (and microbubble solution) such that some of the volume of bioactive agent similarly flows through the permeable region. In other embodiments where the bioactive agent may be coated onto the walls of the balloon 30, the bioactive agent may be released from the walls of the balloon as they expand.

After the balloon 30 is expanded and microbubbles (and bioactive agents) flow out of the permeable region of the balloon 30, ultrasound energy is directed toward the balloon, the volume within the vasculature proximate the balloon and the thrombus, and the tubular region 50 disposed within the internal volume 36 of the balloon 30. The application of the ultrasound energy to the microbubbles present within the ultrasound field F transfers energy to the microbubbles, causing them to vibrate and/or cavitate. The ultrasound energy that engages with the tubular portion 50 is directed toward the balloon (and volume proximate the balloon 30), either by reflection or focusing as aided by the plurality of indentations 52 disposed within the tubular portion, which increases the ultrasound flux available to the microbubbles and therefore cavitation energy present thereon (as well as the percentage of microbubbles energized) to enhance their ability to destroy the thrombus proximate the balloon.

In some embodiments, the ultrasound energy may be applied to the balloon 30, the volume proximate the balloon, and the thrombus with an ultrasound source disposed outside of the anatomy of the patient and manually focused to the intended location. Alternatively, an elongate IVUS device may be threaded through the wire guide lumen 40 of the catheter 20 to be disposed within or proximate the tubular portion 50. The ultrasound energy emitted by the IVUS device passes through and is focused by the tubular portion to increase the cavitation of the microbubbles within and proximate the thrombus.

In embodiments where the device 100 is provided, the device 100 may be positioned proximate an end of a large thrombus, and then the balloon 130 is inflated to substantially occlude the vascular region proximate the thrombus. Microbubble solution (and potentially a bioactive agent) is applied to the internal volume 136, which a portion thereof may escape the balloon 130 through the permeable region 133 disposed on the distal end portion 139 of the balloon 130. The placement of the inflated balloon 130 with respect to the thrombus forms an enclosed volume between the balloon 130 and the thrombus, which concentrates the microbubbles and bioactive agents available to destroy the thrombus, and prevents particles and fluid to flow past the balloon 130 toward the proximal end of the device. The residual dispersed clot can be drawn into a catheter.

In embodiments where devices 200 or 400 are used, the device is positioned within the vasculature as with the embodiments discussed above, and the inner first balloon (230) is inflated toward the expanded position. This inflation also causes the outer second balloon (240, 440) to similarly expand. Microbubble solution (and bioactive agents) may then be introduced into the second volume (246, 446) between the inner surface of the second balloon and the outer surface of the first balloon. Microbubble solution (and in some embodiments bioactive agent) may escape the second balloon through the permeable portion (243, 449) and act upon the thrombus, as discussed above. An external or IVUS ultrasound source may provide an ultrasound energy field to provide energy to the microbubbles to oscillate the same, as aided by the tubular portion 50 disposed with the volume enclosed by the first balloon.

In all embodiments, the procedure continues (with the application of additional microbubbles, bioactive agents, and ultrasound energy) as necessary to destroy, reduce, or remove the desired amount of a thrombus noted within the patient's vasculature. In some embodiments, the procedure is performed to destroy the thrombus in conjunction with a second device (such as a filter, a basket, or the like) disposed downstream of the thrombus (i.e. in the direction of normal blood flow after passing the thrombus) to catch thrombus particles that are removed from the thrombus during the procedure. The thrombus particles caught within the filter, basket, etc. may be removed from the patient's vasculature to avoid those particles ultimately flowing to the patient's heart and/or lungs.

Figure 13:
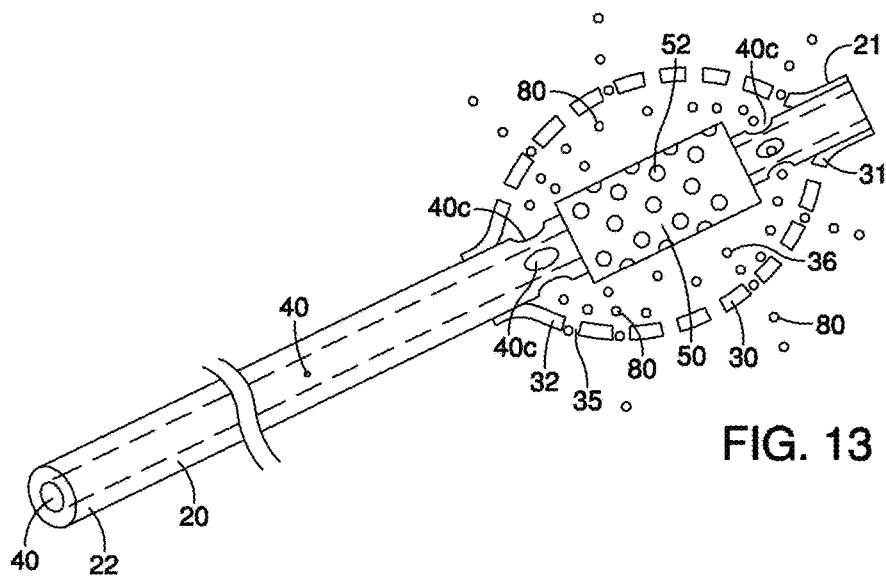
FIG. 13 is an alternate configuration of the device of FIG. 1 in an expanded configuration with a plurality of openings disposed upon the wireguide lumen.
Figure 13A:
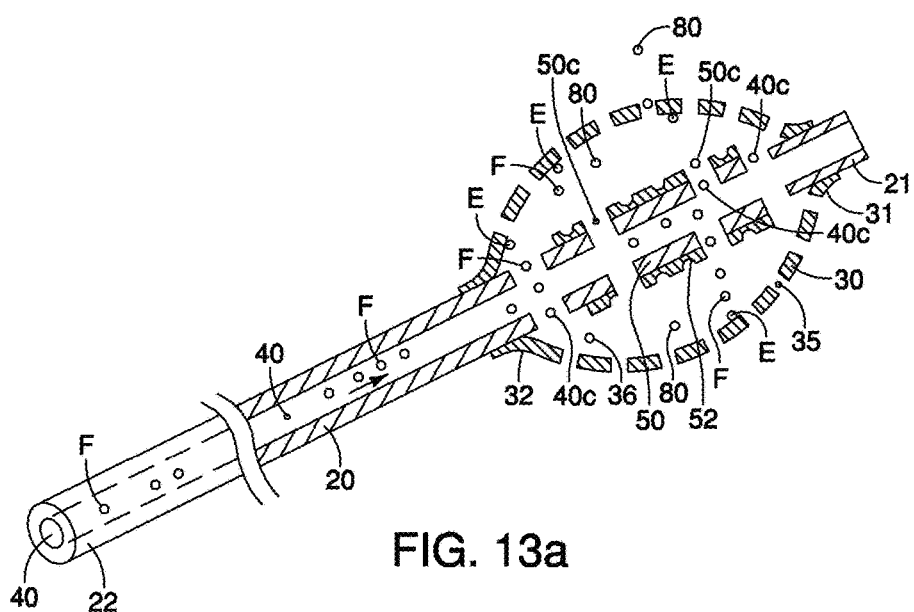
FIG. 13a is partial cross-sectional view of another alternate configuration of the device of FIG. 1 in an expanded configuration where a plurality of openings are disposed upon the tubular member and in registry with a plurality of openings disposed upon the wireguide lumen.

In some or all of the embodiments discussed above, the respective device (e.g. 10, 100, 200, 400) may be of a different orientation such that the respective device include only the wireguide lumen 40, and not the first lumen 38, as shown in FIGS. 13 and 13a. As shown in FIG. 13, the wireguide lumen 40 includes one a plurality of openings 40c that are disposed within the internal volume 36 of the balloon (e.g. balloon 35 of the device 10, other suitable balloons of the other embodiments disclosed herein), such that a portion of fluid that is urged to flow from the proximal end of the catheter 20 through the wireguide lumen 40 enters the internal volume 40 of the balloon 30. In this embodiment, the microbubble solution (as discussed above) may consist of or be included with the fluid flowing through the wireguide lumen 40 such that the microbubble solution assists with expanding the balloon 30.

As discussed with respect to the embodiments above, as the balloon 30 expands to the expanded position due to the increased fluid pressure within the internal volume 36, the plurality of apertures 35 defining the permeable region 33 expand with the expansion of the balloon 30. The microbubbles within the internal volume are small enough such that the microbubbles proximate the apertures 35 flow through the permeable portion 33 and out of the balloon 30, as with the above embodiments. In some embodiments, the one or more openings 40c may be disposed upon the wireguide lumen to direct fluid into the internal volume proximate to but not in-line with the tubular region 50, while in other embodiments, the tubular region 50 may include a plurality of holes 50c that are aligned in registry with openings 40c in the wireguide lumen 40 to allow fluid to flow into the internal volume through the tubular region 50, which may enhance the mixing of the microbubble solution within the entire internal volume 36 of the balloon 30.

It can be understood that the microbubble solution itself may flow into the internal volume 36 of the balloon 30 through the openings 40c in the wireguide lumen 40. In other embodiments, the microbubble solution may be configured or selected to be a product of two or more reagents that are mixed together, or two or more conjugates. In these embodiments as shown schematically in FIG. 13a, one of the reagents E may be coated to or otherwise applied within the balloon 30 (i.e. coated upon the internal surface of the balloon 30, or the outer surface of the wireguide lumen 40), with the other reagent F pumped through the wireguide lumen 40 such that the two reagents E, F or conjugates mix together to form the microbubbles 80 in solution within the internal volume 36 of the balloon 30, just before they are used in the biological or therapeutic process discussed above. This system may be advantageous because it may produce the highest concentration of active microbubbles for use during the process, and may have efficiencies or cost benefits to the design.

It is intended that the foregoing detailed description be regarded as illustrative rather than limiting, and that it be understood that it is the following claims, including all equivalents, that are intended to define the spirit and scope of this invention.

The invention claimed is:

1. A device for clinical therapy, comprising:
an elongate catheter extending between a distal end portion and a proximal end portion, and a first lumen extending through both the distal and proximal end portions and defined by a cylindrical wall within the catheter,
the distal end portion comprising a tubular portion that surrounds the cylindrical wall defining the first lumen within the distal end portion, and a first expandable balloon coaxially surrounding the tubular portion, such that the tubular portion is defined entirely within an interior surface of the first balloon, wherein the tubular portion is echogenic, wherein the tubular portion is defined from a first material and the elongate catheter is defined from a second material, wherein the first material has a greater echogenicity than the second material,
wherein the tubular portion comprises a plurality of indentations defined upon an outer surface thereof, the plurality of indentations are configured to aid in the reflection or focusing of incident ultrasound radiation upon the tubular portion,
wherein the tubular portion further comprises an inner surface that surrounds an outer surface of the cylindrical wall within the elongated catheter, and the tubular portion is fixed to the cylindrical wall;
wherein the elongated catheter is configured to receive an elongate ultrasound probe through the first lumen, with a tip of the probe disposed within the tubular portion, wherein ultrasound energy emitted from the ultrasound probe is focused or reflected by the tubular portion and wherein the tubular portion comprises a helical cut inscribed along at least a portion of a length of the tubular portion.

2. The device of claim 1, wherein the first balloon comprises a permeable portion disposed through walls of the first balloon, such that a portion of fluid disposed within a first volume between an inner surface of the first balloon and an outer surface of the first lumen can escape the first balloon through the permeable portion.

3. The device of claim 1 further comprising an expandable second balloon coaxially surrounding the tubular portion and disposed within the first balloon, wherein the second balloon defines a second volume between an inner surface of the second balloon and the tubular portion, the second volume directly receives fluid or gas through a second lumen to expand both the first and second balloons.

4. The device of claim 2 wherein the permeable portion comprises a plurality of apertures that are configured to expand when the orientation of the first balloon expands outwardly.

5. The device of claim 3 further comprising a third lumen configured to selectively provide fluid communication to a third volume disposed between an inner surface of the first balloon and an outer surface of the second balloon.

6. The device of claim 2 wherein the permeable portion is disposed around an entire outer circumference of the distal portion of the first balloon.

7. The device of claim 2 wherein the permeable portion is disposed only upon a distal portion of the first balloon and not upon central and proximal portions of the first balloon.

8. The device of claim 2 wherein the distal portion of the first balloon is configured such that axes through a plurality of apertures defining the permeable portion in the wall of the first balloon are located such that an angle between a line perpendicular to a tangent line upon an outer surface of the first balloon at the plurality of apertures and the longitudinal axis of the tubular portion forms an angle that is less than or equal to 45 degrees.

9. The device of claim 1 wherein the ultrasound energy emitted from the ultrasound probe is focused or reflected by the tubular portion to impart energy to a plurality of microbubbles proximate the first balloon.

10. The device of claim 1 wherein the first lumen includes a plurality of openings disposed within an internal volume defined by the first balloon, wherein the plurality of openings are configured to direct a portion of fluid flowing through the first lumen to flow into the internal volume.

11. The device of claim 1 further comprising a plurality of holes disposed through the tubular portion and aligned in registry with respective openings disposed upon the first lumen.

12. A method for performing thrombolytic therapy, comprising:
inserting a catheter into and through a patient's vasculature to an area proximate a thrombus, the catheter comprising a distal end portion with an inflatable first balloon defining a first volume therein and comprising a permeable region configured to allow fluid to pass out of the first balloon from the first volume, the catheter further comprising an echogenic tubular portion disposed within the first volume such that the tubular portion is defined entirely within an interior surface of the first balloon, and the tubular portion is fixed to a cylindrical wall within the catheter defining a wire guide lumen, and wherein the tubular portion comprises a helical cut inscribed along at least a portion of a length of the tubular portion, and a proximal end portion defining an inflation lumen providing fluid communication to the first volume, wherein the tubular portion further comprises a plurality of indentations on an outer surface thereof, with the tubular portion further comprising an inner surface that surrounds an outer surface of the cylindrical wall within the catheter defining the wire guide lumen, wherein the tubular portion is defined from a first material and the catheter is defined from a second material, wherein the first material has a greater echogenicity than the second material;

applying a source of fluid to the first volume to expand the first balloon to an expanded configuration;

applying a field of ultrasonic energy to the first balloon and the tubular portion disposed therewithin, wherein the ultrasonic energy field is configured to apply energy to the tubular portion, wherein the tubular portion is configured to reflect or focus the ultrasonic energy received.

13. The method of claim 12, wherein the catheter further comprises an inflatable second balloon disposed within the first volume and surrounded by the first balloon, wherein the tubular portion is disposed within a second volume defined by the second balloon such that the tubular portion is defined within an interior surface of the second balloon, and further comprising a second lumen configured to direct fluid within a third volume outside of an outer surface of the second balloon and within an inner surface of the first balloon.

14. The method of claim 12, wherein the permeable region is disposed upon a distal end portion of the first balloon and not disposed upon a central portion and a proximal end portion of the first balloon.

15. The method of claim 12, wherein the tubular portion is an elongate cylindrical member and the plurality of indentations being positioned in spaced relationships about an entire outer surface of the tubular member wherein the plurality of indentations each extend radially inward through a portion of a thickness of a wall defining the tubular portion, wherein the tubular member further comprises a helical cut along a length of the tubular member.

16. The device of claim 1, wherein the plurality of indentations each extend radially inward through a portion of a thickness of a wall defining the tubular portion.

17. The device of claim 1, wherein the indentations are arranged upon the tubular portion in a plurality of rows, with centers of the indentations within of one row aligned with a space between neighboring indentations within a neighboring row.

18. The device of claim 1, wherein the plurality of indentations are each 0.07 mm in diameter and are disposed with a spacing of 0.234 mm between neighboring dimples.

19. The device of claim 1, wherein the plurality of indentations are formed with a conical profile at an arc of 30 degrees.

20. The device of claim 1, wherein the tubular portion is metal.

21. A device for clinical therapy, comprising:
an elongate catheter extending between a distal end portion and a proximal end portion, and a first lumen extending through both the distal and proximal end portions and defined by a cylindrical wall within the elongated catheter, the distal end portion comprising a tubular portion that surrounds the cylindrical wall defining the first lumen within the distal end portion, and a first expandable balloon coaxially surrounding the tubular portion, such that the tubular portion is defined entirely within an interior surface of the first balloon, wherein the tubular portion is echogenic, wherein the tubular portion is defined from a first material and the elongate catheter is defined from a second material, wherein the first material has a greater echogenicity than the second material, wherein the tubular portion comprises a plurality of indentations defined upon an outer surface thereof, the plurality of indentations are configured to aid in the reflection or focusing of incident ultrasound radiation upon the tubular portion, wherein the tubular portion further comprises an inner surface that surrounds an outer surface of the cylindrical wall within the elongated catheter;

wherein the tubular portion comprises a helical cut inscribed along at least a portion of a length of the tubular portion;

wherein the indentations are arranged upon the tubular portion in a plurality of rows, with centers of the indentations within of one row aligned with a space between neighboring indentations within a neighboring row;

wherein the plurality of indentations are each 0.07 mm in diameter and are disposed with a spacing of 0.234 mm between neighboring dimples;

wherein the plurality of indentations are formed with a conical profile at an arc of 30 degrees, wherein the elongated catheter is configured to receive an elongate ultrasound probe through the first lumen, with a tip of the elongated ultrasound probe disposed within the tubular portion, wherein ultrasound energy emitted from the elongated ultrasound probe is focused or reflected by the tubular portion to impart energy.

22. The method of claim 12, further comprising the step of the step of providing a plurality of microbubbles within the first volume that may escape the first volume through the permeable region when the first volume is in the expanded configuration, and the step of applying a field of ultrasonic energy to the first balloon and the tubular portion disposed therein further comprises applying energy to the tubular portion transfers the plurality of microbubbles to a cavitating state.

* * * * *

UNITED STATES PATENT AND TRADEMARK OFFICE
CERTIFICATE OF CORRECTION

PATENT NO. : 10,226,264 B2
APPLICATION NO. : 13/555685
DATED : March 12, 2019
INVENTOR(S) : Charles L. McIntosh et al.

It is certified that error appears in the above-identified patent and that said Letters Patent is hereby corrected as shown below:

In the Claims

At Claim 22, Column 20, Line 42, after "comprising", delete "the step of"

Signed and Sealed this
Fourteenth Day of May, 2019

Andrei Iancu
*Director of the United States Patent and Trademark Office*